United States Patent
Yan et al.

(10) Patent No.: US 11,382,921 B2
(45) Date of Patent: Jul. 12, 2022

(54) USE OF COMPOUNDS IN PREPARATION OF A MEDICAMENT FOR TREATMENT OF HEMORRHAGIC STROKE

(71) Applicant: GUANGZHOU CELLPROTEK PHARMACEUTICAL CO., LTD, Guangdong (CN)

(72) Inventors: Guangmei Yan, Guangdong (CN); Yijun Huang, Guangdong (CN); Wei Yin, Guangdong (CN); Suizhen Lin, Guangdong (CN)

(73) Assignee: GUANGZHOU CELLPROTEK PHARMACEUTICAL CO., LTD, Guangdong (CN)

( * ) Notice: Subject to any disclaimer, the term of this patent is extended or adjusted under 35 U.S.C. 154(b) by 193 days.

(21) Appl. No.: 16/958,575

(22) PCT Filed: Dec. 28, 2018

(86) PCT No.: PCT/CN2018/124707
§ 371 (c)(1),
(2) Date: Jun. 26, 2020

(87) PCT Pub. No.: WO2019/129181
PCT Pub. Date: Jul. 4, 2019

(65) Prior Publication Data
US 2021/0060035 A1 Mar. 4, 2021

(30) Foreign Application Priority Data

Dec. 29, 2017 (CN) .......................... 201711479490.8

(51) Int. Cl.
*A61K 9/08* (2006.01)
*A61K 9/10* (2006.01)
*A61K 9/19* (2006.01)
*A61K 31/56* (2006.01)
*A61K 31/565* (2006.01)
*A61K 31/568* (2006.01)
*A61K 31/575* (2006.01)
*A61K 47/40* (2006.01)
*A61P 7/04* (2006.01)
*A61P 9/00* (2006.01)
*A61P 25/00* (2006.01)
*C07J 1/00* (2006.01)
*C07J 3/00* (2006.01)
*C07J 7/00* (2006.01)
*C07J 9/00* (2006.01)
*A61P 9/10* (2006.01)

(52) U.S. Cl.
CPC .............. *A61K 31/568* (2013.01); *A61P 9/10* (2018.01)

(58) Field of Classification Search
CPC ... A61K 9/08; A61K 9/10; A61K 9/19; A61K 31/56; A61K 31/565; A61K 31/568; A61K 31/575; A61K 47/40; A61P 7/04; A61P 9/00; A61P 25/00; C07J 1/0007; C07J 3/00; C07J 7/0005; C07J 9/00
See application file for complete search history.

(56) References Cited

U.S. PATENT DOCUMENTS

2013/0157993 A1  6/2013  Yan et al.
2014/0127185 A1  5/2014  Stein et al.

FOREIGN PATENT DOCUMENTS

| CN | 101472579 A | 7/2009 |
| CN | 101683348 A | 3/2010 |
| CN | 101884638 A | 11/2010 |
| CN | 101961311 A | 2/2011 |
| CN | 102180928 B | 1/2013 |
| CN | 104288110 A | 1/2015 |
| EP | 2 620 153 A1 | 7/2013 |
| WO | WO-2008/039566 A2 | 4/2008 |

OTHER PUBLICATIONS

Carlos S. Kase, "Intracerebral Hemorrhage: Non-Hypertensive Causes", Progress Reviews, Stroke, vol. 17, No. 4, 1986, pp. 590-595 (6 pages).
Chamorro et al., Neuroprotection in acute stroke: targeting excitotoxicity, oxidative and nitrosative stress, and inflammation, Lancet Neurol, 2016, vol. 15, pp. 869-881 (13 pages).
G. Chen et al., "Expression of NR2B in Different Brain Regions and Effect of NR2B Antagonism on learning Deficits After Experimental Subarachnoid Hemorrhage", Neuroscience, 2013, pp. 136-144 (9 pages).
Hwang et al., "Advances in Neuroprotective Strategies: Potential Therapies for Intracerebral Hemorrhage", Cerebrovasular Diseases, 2011, vol. 31, pp. 211-222 (12 pages).
Jiesi Chen, et al., "A synthetic steroid 5alpha-androst-3b,5,6beta-triol blocks hypoxia/reoxygenation-induced neuronal injuries via protection of mitochondrial function", Steroids, vol. 78, 2013, pp. 996-1002 (7 pages).
O'Collins et al., "1,026 Experimental Treatments in Acute Stroke", Ann Neurol, 2006, vol. 56, pp. 467-477 (11 pages).
English Translation of International Search Report and Written Opinion issued in PCT Application No. PCT/CN2018/124707 dated Mar. 14, 2019, 3 pages.
International Search Report and Written Opinion issued in PCT Application No. PCT/CN2018/124707 dated Mar. 14, 2019, 9 pages.
Wang et al., "Glial cells and cerebral hemorrhage", Letter in Biotechnology, vol. 28, No. 5, Sep. 30, 2017, 5 pages.
Yan et al., "Neuroprotectant Androst-3β, 5α, 6β-Triol Suppresses TNF-α-Induced Endothelial Adhesion Molecules Expression and Neutrophil Adhesion to Endothelial Cells by Attenuation of CYLD-NF-KB Pathway", Biochemical and Biophysical Research Communications, vol. 483, Jan. 9, 2017, pp. 892-896.

(Continued)

*Primary Examiner* — Brenda L Coleman
(74) *Attorney, Agent, or Firm* — Foley & Lardner LLP

(57) ABSTRACT

Disclosed is a use of 5α-androstane-3β,5,6β-triol, an analogue, a deuterated derivative, and a pharmaceutically acceptable salt thereof in manufacture of a medicament for the treatment of hemorrhagic stroke in a patient. The hemorrhagic stroke is intracerebral hemorrhage or subarachnoid hemorrhage.

18 Claims, 3 Drawing Sheets

(56) References Cited

OTHER PUBLICATIONS

Takehiro, Nakamura, et al.; "Acute Phase Management (2) Possibility of New Drug Therapy"; Molecular Cerebrovascular Medicine, vol. 12, No. 3; dated Jul. 1, 2013; pp. 256-261.

A.

B.

USE OF COMPOUNDS IN PREPARATION OF A MEDICAMENT FOR TREATMENT OF HEMORRHAGIC STROKE

CROSS-REFERENCE TO RELATED APPLICATIONS

This application is a national stage entry under 35 U.S.C. § 371 of International Patent Application No. PCT/CN2018/124707 filed Dec. 28, 2018, which in turn claims priority to Chinese Application No. 201711479490.8, filed Dec. 29, 2017, the entire content of each of which are hereby incorporated by reference.

TECHNICAL FIELD

The present invention relates to a novel medical use of 5α-androst-3β,5,6β-triol (Triol) and analogue thereof, and in particular to the use of these compounds in the treatment of hemorrhagic stroke.

BACKGROUND

Stroke is an acute cerebrovascular disease caused by brain tissue injury as a result of sudden rupture of brain blood vessels or inability of blood flow to the brain due to blood vessels blockage, including ischemic cerebral stroke and hemorrhagic stroke. According to statistical data from WHO in 2014, cerebrovascular accidents, mainly as stroke, have the second highest mortality rate in the world, and are major cause of severe disability and dementia worldwide. Global death due to cerebrovascular diseases in 2015 was 6.326 million, including 2.978 million ischemic strokes and 3.348 million hemorrhagic or other strokes.

Ischemic stroke refers to a sudden occurrence of local blood supply failure in the brain tissue due to various reasons, resulting in lesions and necrosis of cerebral ischemic hypoxic, which further leads to clinically corresponding diseases of neurological function deficit. Depending on the pathogenesis, the main types of ischemic stroke include thrombotic cerebral infarction, embolic cerebral infarction, lacunar cerebral infarction, multiple cerebral infarctions, transient ischemic attack (TIA) and so on.

Unlike ischemic stroke, hemorrhagic stroke, also called as encephalorrhagia or cerebral hemorrhage, is a series of clinical manifestations of neurological dysfunction resulting from rupture of intracranial blood vessels and leakage of blood into the brain. Hemorrhagic stroke has a higher mortality rate in the acute phase than that of ischemic stroke. Hemorrhagic strokes are mainly classified as intracerebral hemorrhage (ICH) and subarachnoid hemorrhage (SAH), depending on the different bleeding sites in the brain tissue. ICH and SAH can occur concurrently. ICH refers to bleeding caused by rupture of blood vessels in the brain parenchyma, and SAH is a general term for bleeding caused by various reasons that occurs between the pia mater and the arachnoid with blood flowing into the subarachnoid space. Hypertension is the most common cause of non-traumatic ICH, and followed by cerebrovascular malformation, cerebral amyloid angiopathy, aneurysm, moyamoya disease, cerebral arteritis, primary or metastatic tumor, surgery, ischemic stroke, infarction, thrombolysis or anticoagulation therapy and so on. The common cause of SAH is intracranial aneurysm, and followed by cerebrovascular malformations and hypertensive arteriosclerosis. SAH can also be found in arteritis, abnormal vascular network of the pavimentum cerebri, connective tissue diseases, blood diseases, anticoagulation therapy and so on. SAH is the most common cause of sudden death from stroke.

Central nervous system injury may be also caused by surgery, which refers to the direct injury to the nervous tissue during surgical operation performed in the central nervous system (including the brain and notochord) and istopathological changes (including tissue edema, bleeding, microbleeds, infarction and microinfarction) of the nervous system caused by changes in blood supply and bleeding during the operation. Common surgeries that cause central nervous system injury include, but are not limited to, intracranial aneurysmal clipping or embolization, brain tumor resection, and other surgeries that directly involve the central nervous system.

Different types of stroke require different treatments, or even the opposite. Methods to distinguish between ischemic and hemorrhagic strokes are known in the art, for example as described in PCT/EP2015/078576 and PCT/US2007/073272. Due to the lack of effective treatments, prevention is currently considered the best measure. Therefore, it is of great clinical significance to provide a drug for the treatment of hemorrhagic stroke. In recent years, with the development of interdisciplinary subjects such as neuroimaging, the diagnosis of acute stroke is more accurate and faster, and it is more beneficial to the choice of treatment plan and prognosis judgment, but so far there has not been an independent treatment method that can cure stroke.

SUMMARY

In one aspect, the present invention provides use of a compound of formula I, a deuterated analog, or a pharmaceutically acceptable salt thereof in the manufacture of a medicament for the treatment of hemorrhagic stroke,

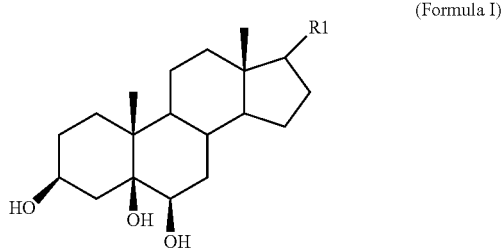

(Formula I)

wherein $R_1$ is H, an alkyl or terminal alkenyl having 1 to 5 carbon atoms, or —CH(CH$_3$)(CH$_2$)$_3$CH(CH$_3$)$_2$.

In one embodiment, wherein $R_1$ is preferably H, and the compound is 5α-androst-3β,5,6β-triol (also referred to as Triol hereinafter). In one embodiment, $R_1$ is selected from a group consisting of —CHCH$_2$CH$_3$, —CH(CH$_3$)$_2$, —CH(CH$_2$)$_3$CH$_3$ and —CH(CH$_3$)(CH$_2$)$_3$CH(CH$_3$)$_2$.

In another aspect, the present invention provides a method for treating hemorrhagic stroke in a patient, comprising administrating to the patient an effective amount of a compound of formula I, a deuterated analog, or a pharmaceutically acceptable salt thereof; or a pharmaceutical composition comprising the compound of formula I or a deuterated compound or a pharmaceutically acceptable salt thereof;

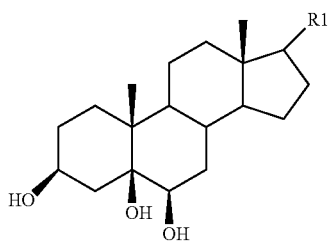

(Formula I)

wherein R₁ is H, an alkyl or terminal alkenyl having 1 to 5 carbon atoms, or —CH(CH₃)(CH₂)₃CH(CH₃)₂.

In one embodiment, wherein R₁ is preferably H. In one embodiment, R₁ is selected from a group consisting of —CHCH₂CH₃, —CH(CH₃)₂, —CH(CH₂)₃CH₃ and —CH(CH₃)(CH₂)₃CH(CH₃)₂.

In a further aspect, the present invention provides a compound of formula I, a deuterated analog, or a pharmaceutically acceptable salt thereof for use in the treatment of hemorrhagic stroke in a patient,

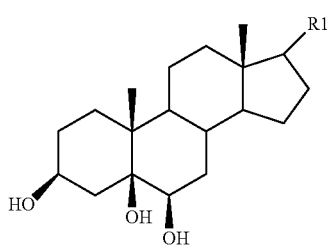

(Formula I)

wherein R₁ is H, an alkyl or terminal alkenyl having 1 to 5 carbon atoms, or —CH(CH₃)(CH₂)₃CH(CH₃)₂.

In one embodiment, wherein R₁ is preferably H. In one embodiment, R₁ is selected from a group consisting of —CHCH₂CH₃, —CH(CH₃)₂, —CH(CH₂)₃CH₃ and —CH(CH₃)(CH₂)₃CH(CH₃)₂.

In some embodiments, the intracerebral stroke manifests as blood outflowing caused by fracture or breakage of vessel in brain tissue.

In some embodiments, the hemorrhagic stroke is intracerebral hemorrhage (ICH) such as hypertensive intracerebral hemorrhage. In some embodiments, the intracerebral hemorrhage is intracerebral hemorrhage caused by cerebrovascular malformation, cerebral amyloid angiopathy, aneurysm, moyamoya disease, cerebral arteritis, primary or metastatic tumor, ischemic stroke infarction, surgery, or thrombolytic or anticoagulant therapy.

In some embodiments, the hemorrhagic stroke is subarachnoid hemorrhage (SAH), such as a subarachnoid hemorrhage caused by intracranial aneurysm. In other embodiments, the subarachnoid hemorrhage is a subarachnoid hemorrhage caused by cerebrovascular malformation, hypertensive arteriosclerosis, arteritis, abnormal vascular network at the base of brain, connective tissue disease, blood disease, surgery, or anticoagulation therapy.

In some embodiments, the hemorrhagic stroke is the complication of the intracerebral hemorrhage and subarachnoid hemorrhage, including but not limited to, the complication of intracerebral hemorrhage and subarachnoid hemorrhage caused by hypertension, cerebrovascular malformation, ischemic stroke infarction, brain amyloid angiopathy, aneurysm, moyamoya disease, cerebral arteritis, primary or metastatic tumor, hypertensive arteriosclerosis, arteritis, abnormal vascular network of pavimentum cerebri, connective tissue disease, blood disease, surgery, intracranial aneurysm, or thrombolysis or anticoagulation treatment.

In some embodiments, the hemorrhagic stroke is caused by surgery. In some embodiments, the hemorrhagic stroke is intracerebral hemorrhage (ICH) caused by surgery, subarachnoid hemorrhage (SAH) caused by surgery, or a complication of both. In some embodiments, the surgery is referred to a surgery directly involving the central nervous system. In some embodiments, the surgery is referred to intracranial aneurysmal clipping or embolization, or brain tumor resection.

In some embodiments, the medicament further includes additional therapeutic agents.

In some embodiments, the patient is a human patient.

DETAILED DESCRIPTION OF THE INVENTION

Figure 1:
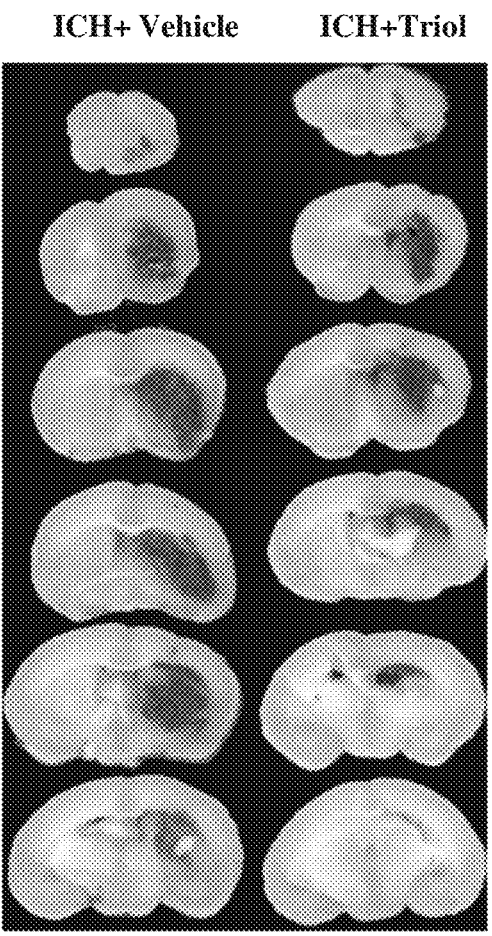
FIG. 1. The amount of cerebral hemorrhage is significantly reduced by Triol in the C57B mouse model of cerebral hemorrhage. A. Representative brain slice at 24 h after cerebral hemorrhage; B. The amount of intracerebral hemorrhage at 24 h, n=10 in each group, **p<0.01.
Figure 1:
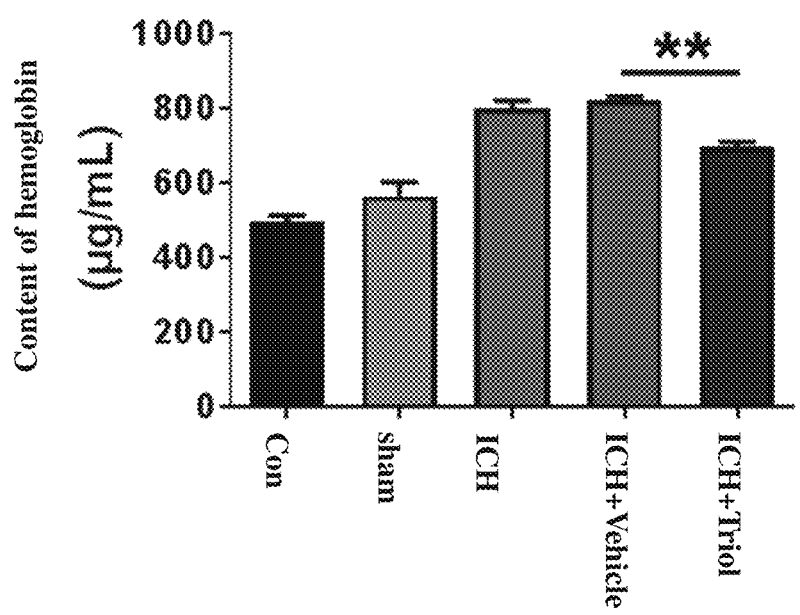

As used herein, the term "composition" refers to a formulation suitable for administration to an expected animal subject for therapeutic purposes, which comprises at least one pharmaceutically active component, such as a compound. Optionally, the composition further comprises at least one pharmaceutically acceptable carrier or excipient.

The term "pharmaceutically acceptable" means that the substance does not have the property that, considering the disease or condition to be treated and the respective route of administration, will allow rational and prudent medical practitioners to avoid administering the substance to the patient. For example, for injectables, it is often required that such substance is substantially sterile.

As used herein, the terms "therapeutically effective amount" and "effective amount" mean that the substance and the amount of the substance are effective to prevent, alleviate or ameliorate one or more symptoms of a disease or condition, and/or prolong the survival of the subject receiving the treatment.

As used herein, "treatment" includes the administration of a compound of the present application or a pharmaceutically acceptable salt thereof to alleviate the symptoms or complications of a disease or condition, or to eliminate the disease or condition. The term "alleviate" as used herein is used to describe the process of reducing the severity of signs or symptoms of a disorder. Symptoms can be alleviated but not eliminated. In one embodiment, administration of the pharmaceutical composition of the present application results in the elimination of signs or symptoms.

The term "intracerebral stroke caused by surgery" refers to intracerebral hemorrhage or subarachnoid hemorrhage, or a complication of both, due to surgery operation.

Compound of Formula I, a Deuterated Analog, or a Pharmaceutically Acceptable Salt Thereof Compounds available for the method or the use of the present invention comprise a compound of formula I, a deuterated analog, or a pharmaceutically acceptable salt thereof,

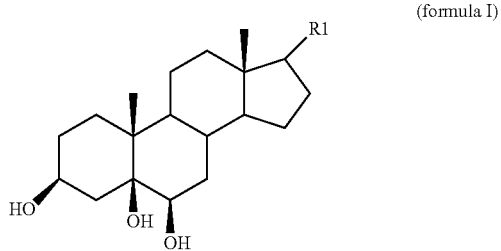

(formula I)

wherein $R_1$ is H, an alkyl or terminal alkenyl having 1 to 5 carbon atoms, or —$CH(CH_3)(CH_2)_3CH(CH_3)_2$, and is also referred to as "compounds of the present invention". In one embodiment, $R_1$ is H and the compound is 5α-androst-3β,5,6β-triol (also referred as to Triol hereinafter), having the structure of formula II.

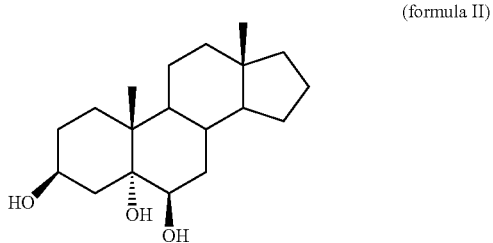 [SMILES: C[C@@]12CCCC1C1C[C@@H](O)[C@@]3(O)C[C@@H](O)CC[C@]3(C)C1CC2]

(formula II)

It has been confirmed that Triol is a neuron protective agent effective against acute ischemic hypoxic brain damage.

In one embodiment, $R_1$ is -$CHCH_2CH_3$, and the compound is 17-propylidene-androst-3β,5,6β-triol. In one embodiment, $R_1$ is —$CH(CH_3)_2$, and the compound is 17-isopropyl-androst-3β,5,6β-triol. In one embodiment, $R_1$ is —$CH(CH_2)_3CH_3$, and the compound is 17-butyl-androst-3β,5,6β-triol. In one embodiment, $R_1$ is —$CH(CH_3)(CH_2)_3 CH(CH_3)_2$, and the compound is cholestane-3β,5,6β-triol.

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

The present invention is also intended to include the use of pharmaceutically acceptable deuterated compounds or other non-radioactive substituted compounds. Deuteration is to replace one or more or all of the hydrogen in the active molecular group of the drug with isotope deuterium.

Because it is non-toxic and non-radioactive, and it is about 6-9 times more stable than the carbon-hydrogen bond, it can close the metabolic site and prolong the half-life of the drug, thereby reducing the therapeutic dose without affecting the pharmacological activity of the drug, thus it is considered to be an excellent modification method.

Pharmaceutical Composition

Another aspect of the present invention provides a pharmaceutical composition comprising an effective amount of a compound of formula I, or a deuterated compound or a pharmaceutically acceptable salt thereof, and a pharmaceutically acceptable carrier.

In the present invention, "pharmaceutical composition" refers to a composition comprising a compound of formula I and a pharmaceutically acceptable carrier, wherein the compound and the pharmaceutically acceptable carrier are present in the composition in a mixed form. The composition will generally be used in the treatment of human subjects. However, they can also be used to treat similar or same conditions in other animal subjects.

In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, injections or lyophilized powder injections are preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, preferably 0.1 and 20 mg/kg of the subject being treated. Multiple doses may be used.

The compounds of the invention may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In some embodiments, the present invention provides for delivery of compounds of the invention and one or more other drug therapeutics delivered by a different route of administration or by the same route of administration.

The use in combination for any route of administration includes delivery of compounds of the invention and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes.

Co-administration of separate formulations includes co-administration by delivery via one device, for example the same inhalant device, the same syringe, etc., or administration from separate devices within a short time of each other. Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

Therapeutic Method and Use Thereof

Another aspect of the present invention provides use of the compound of formula I, deuterated analog or a pharmaceutically acceptable salt thereof in manufacture of a medicament for the treatment of hemorrhagic stroke. Accordingly, the present invention provides the compound of formula I, deuterated counterpart or a pharmaceutically acceptable salt thereof for use in the treatment of hemorrhagic stroke. Accordingly, the present invention provides a method for treating a hemorrhagic stroke in a patient, the method comprising administering to the patient an effective amount of a compound of formula I, deuterated analog, or a pharmaceutically acceptable salt thereof; or the pharmaceutical composition as described above.

In some embodiments, the intracerebral stroke manifests as blood outflowing caused by fracture or breakage of vessel in brain tissue.

In some embodiments, the hemorrhagic stroke is intracerebral hemorrhage (ICH) such as hypertensive intracerebral hemorrhage. In some embodiments, the intracerebral hemorrhage is an intracerebral hemorrhage caused by cerebrovascular malformation, cerebral amyloid angiopathy, aneurysm, moyamoya disease, cerebral arteritis, primary or metastatic tumor, ischemic stroke infarction, surgery, or thrombolytic or anticoagulant therapy.

In some embodiments, the hemorrhagic stroke is subarachnoid hemorrhage (SAH), such as a subarachnoid hemorrhage caused by intracranial aneurysm. In other embodiments, the subarachnoid hemorrhage is a subarachnoid hemorrhage caused by cerebrovascular malformation, hypertensive arteriosclerosis, arteritis, abnormal vascular network of pavimentum cerebri, connective tissue disease, blood disease, surgery, or anticoagulation therapy.

In some embodiments, the hemorrhagic stroke is the complication of the intracerebral hemorrhage and subarachnoid hemorrhage, including but not limited to, the complication of intracerebral hemorrhage and subarachnoid hemorrhage caused by hypertension, cerebrovascular malformation, ischemic stroke infarction, brain amyloid angiopathy, aneurysm, moyamoya disease, cerebral arteritis, primary or metastatic tumor, hypertensive arteriosclerosis, arteritis, abnormal vascular network of pavimentum cerebri, connective tissue disease, blood disease, surgery, intracranial aneurysm, or thrombolysis or anticoagulation treatment.

In some embodiments, the hemorrhagic stroke is caused by surgery. In some embodiments, the hemorrhagic stroke is intracerebral hemorrhage (ICH) caused by surgery, subarachnoid hemorrhage (SAH) caused by surgery, or a complication of both. In some embodiments, the surgery is referred to a surgery directly involving the central nervous system. In some embodiments, the surgery is referred to intracranial aneurysmal clipping or embolization, or brain tumor resection.

In some embodiments, the medicament further includes additional therapeutic agents.

In some embodiments, the subject/patient is human.

Example

Experimental Animals:

112 clean grade health C57 male mice (8~10 week, 20-22 g) were purchased from Beijing Vital River Laboratory Animal Technology Co. Ltd. Feeding conditions: 22° C.~26° C., humidity 50%~60%. The mice were grouped, fed with standard feed and purified water, and subjected to adaptive feeding for 1 week.

Reagent and Consumables:

main reagents and consumable instruments: type V collagenase (Sigma, USA), Triol (Guangzhou Cellprotek Pharmaceutical Co., Ltd), hemoglobin detection kit (Drabkins reagent: sodium bicarbonate 1.0 g, potassium hydride 0.05 g, potassium ferricyanide 0.2 g, and distilled added to 1000 ml, store at 4° C.), Enflurane, chloral hydrate, bone wax, micro-injection needle, TES buffer, calcium chloride, perfusate, disposable syringe, cryo vial and so on.

Establishment of Intracerebral Hemorrhage Model and Administration:

Establishment of Intracerebral hemorrhage model: After weighing body weight of mice, anesthesia was induced by 5% enflurane, and maintained by 2% enflurane mixed with 70% $N_2O$ and 30% $O_2$. Mice were fixed on a stereotactic apparatus in the prone position and disinfected topically. The skin of the animals was incised to expose the skull for drilling. 0.3 μl of 0.35UVII collagenase was slowly injected with a micro sampler. The needle was kept for 5 min then slowly pulled out for 5 min, and the skull drilling was covered by bone glue. Animals were sutured, and subjected to routine disinfection. In the sham operation group, the needle was inserted in the same way, but without injection. The solvent or Triol was administered by intraperitoneal injection at 60 mg/kg 1 h after modeling.

Animal Grouping:

C57 mice were divided into 5 groups using random number method, namely normal control group (n=12), sham operation group (n=12), cerebral hemorrhage group (n=26), cerebral hemorrhage+solvent intraperitoneal injection 1 h after modeling group (n=26), and cerebral hemorrhage+Triol intraperitoneal injection 1 h after modeling group (n=26).

Neurobehavioral Scoring:

The neurological function was measured 24 hours after the cerebral hemorrhage model was established.

Determination of Intracerebral Hemorrhage:

chloral hydrated peritoneal was injected intraperitoneally for anesthesia at 24 hours after modeling. After transcardial perfusion with PBS, the brain was immediately removed, and the hemorrhage side of the brain was cut off. It was rinsed with normal saline to remove the blood at the outer surface and homogenized, and the supernatant was collected and stored. The hemoglobin content in the brain was measured with a hemoglobin detection kit.

Results

The Amount of Cerebral Hemorrhage is Significantly Reduced by Triol in C57B Mice of Cerebral Hemorrhage Model Various treatments were performed at 1 h after intracranial hemorrhage induced by intracranial injection of collagenase in C57B mice. The hemorrhage area (volume) of the hemisphere brain with collagenase injection was significantly reduced by Triol (FIG. 1A) 24 h later. Through the determination of hemoglobin content, it can be seen that the hemoglobin content of the hemorrhagic hemisphere treated with Triol, that is, the amount of hemorrhage, decreased significantly as compared with the cerebral hemorrhage model group (p<0.01) (FIG. 1B). The above data shows that Triol can effectively reduce cerebral hemorrhage.

Figure 2:
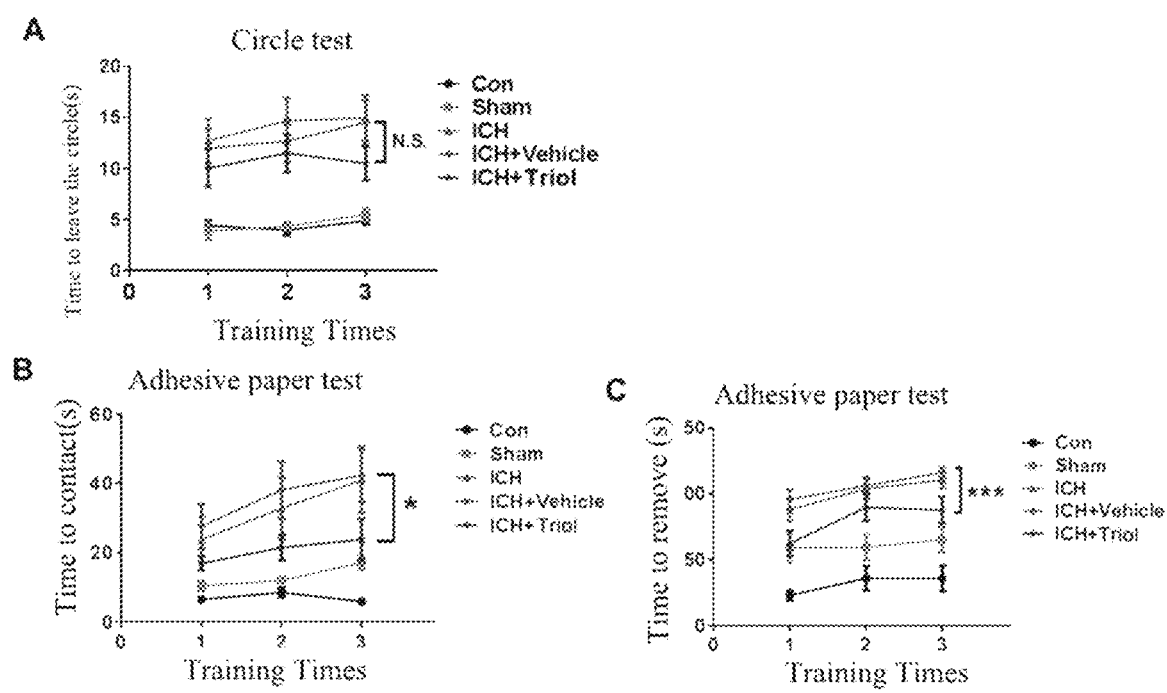
FIG. 2. Neurosensory function is significantly improved by Triol in C57B mice after cerebral hemorrhage. A. Circle test; Adhesive paper test; B. Time duration for contacting adhesive paper; C. Time consumption to tear off adhesive paper; *p<0.05, ***p<0.001, n=12~23 animals/group. con: normal; sham: sham-operated group; ICH: cerebral hemorrhage model; vehicle: solvent.

Neurosensory Function is Significantly Improved by Triol after Cerebral Hemorrhage in C57B Mice After 24 hours of intracerebral hemorrhage induced by collagenase injection, all of sensory functions of C57B mice were greatly inactivated. After administration with Triol, the time taken for the mice to go out of the center of the circle to any point of the circle edge has a tendency to decrease, indicating that Triol has restored the sense of orientation of the mice with cerebral hemorrhage (FIG. 2A). In the adhesive paper test, the time duration for contacting adhesive paper (p<0.05) and the time consumption to remove adhesive paper (p<0.001) in mice with cerebral hemorrhage was significantly reduced by Triol. Therefore, the sense of touch at the body surface of mice damaged by cerebral hemorrhage was significantly improved (FIG. 2B, 2C).

Somatosensory and Motor Function is Significantly Improved by Triol after Cerebral Hemorrhage in C57B Mice.

Figure 3:
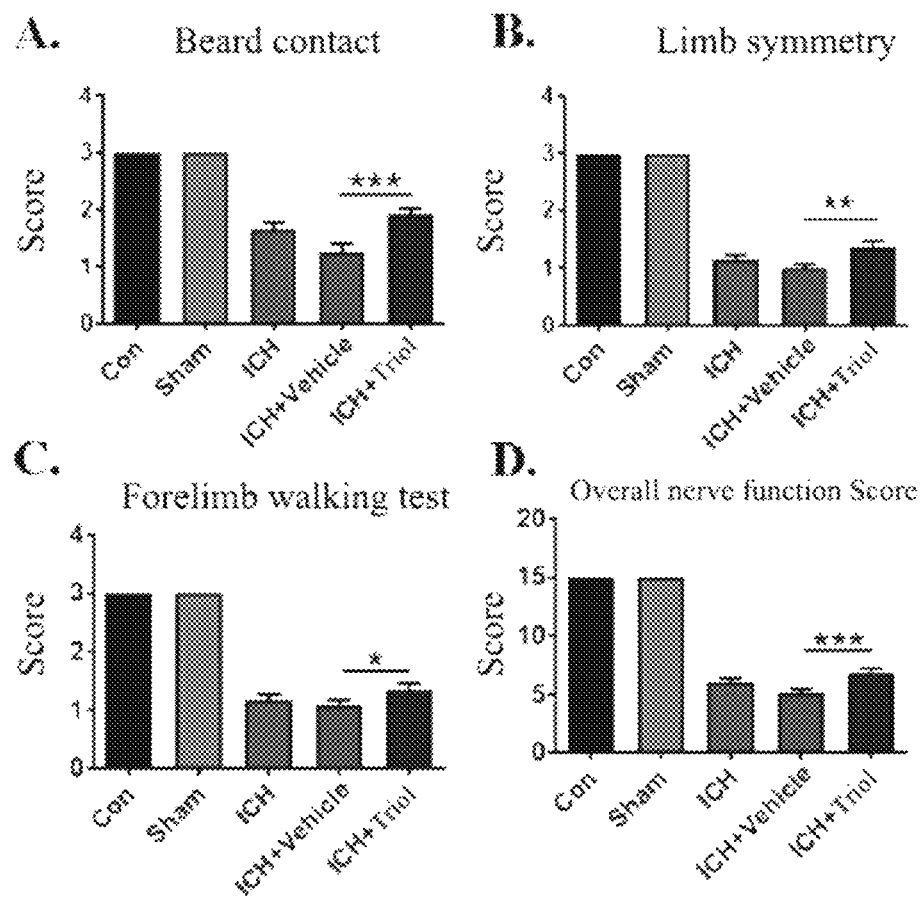
FIG. 3. Somatosensory and motor function is significantly improved by Triol after cerebral hemorrhage in C57B mice. Modified Garcia score (A-D) is used to evaluate somatosensory and motor function at 24 hours after cerebral hemorrhage in C57B mice: A. Nose hair contact test; B. Limb symmetry test; C. Forelimb walking test, D. Overall nerve function Score; n=12~23 animals/group, *p<0.05, p<0.01, *p<0.001. con: normal; sham: sham-operated group; ICH: cerebral hemorrhage model; vehicle: solvent.

Twenty-four hours after intracerebral hemorrhage induced by collagenase injection, the somatosensory and motor function of C57B mice was obviously inactivated. However, after administration with Triol, the beard touch avoidance of the mice was significantly restored, indicating that the fine tactile response movement of the mice with cerebral hemorrhage (p<0.001) (FIG. 3A) was significantly improved by Triol. After treatment administration with Triol, symmetry of the limbs' movement (p<0.01) (FIG. 3B) and forelimb walking of mice (p<0.05) (FIG. 3C) were significantly improved, indicating that the proprioception and motor control function of mice damaged by cerebral hemorrhage were restored by Triol. In terms of comprehensive evaluation, neurological function scores in mice with cerebral hemorrhage was significantly improved by Triol (p<0.001) (FIG. 3D).

The invention claimed is:

1. A method for treating hemorrhagic stroke in a subject, the method comprising administrating to the subject an effective amount of a compound of formula I, a deuterated analog or a pharmaceutically acceptable salt thereof,

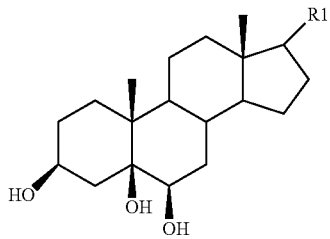

(Formula I)

wherein $R_1$ is H, an alkyl or terminal alkenyl having 1 to 5 carbon atoms, or —CH(CH$_3$)(CH$_2$)$_3$CH(CH$_3$)$_2$.

2. The method of claim 1, wherein $R_1$ is H.

3. The method of claim 1, wherein $R_1$ is selected from a group consisting of =CHCH$_2$CH$_3$, —CH(CH$_3$)$_2$, and —CH(CH$_3$)(CH$_2$)$_3$CH(CH$_3$)$_2$.

4. The method of claim 1, wherein the hemorrhagic stroke is intracerebral hemorrhage (ICH).

5. The method of claim 4, wherein the intracerebral hemorrhage is hypertensive intracerebral hemorrhage.

6. The method of claim 4, wherein the intracerebral hemorrhage is an intracerebral hemorrhage caused by cerebrovascular malformation, cerebral amyloid angiopathy, aneurysm, moyamoya disease, cerebral arteritis, primary or metastatic tumor, ischemic stroke infarction, surgery, or thrombolytic or anticoagulant therapy.

7. The method of claim 1, wherein the hemorrhagic stroke is subarachnoid hemorrhage.

8. The method of claim 7, wherein the subarachnoid hemorrhage is a subarachnoid hemorrhage caused by intracranial aneurysm.

9. The method of claim 7, wherein the subarachnoid hemorrhage is a subarachnoid hemorrhage caused by cerebrovascular malformation, hypertensive arteriosclerosis, arteritis, abnormal vascular network of pavimentum cerebri, connective tissue disease, blood disease, surgery, or anticoagulation therapy.

10. The method of claim 1, wherein the hemorrhagic stroke is a complication of intracerebral hemorrhage (ICH) and subarachnoid hemorrhage (SAH).

11. The method of claim 1, wherein the hemorrhage stroke is caused by surgery.

12. The method of claim 11, wherein the hemorrhage stroke caused by surgery is an intracerebral hemorrhage cause by surgery.

13. The method of claim 11, wherein the hemorrhage stroke caused by surgery is a subarachnoid hemorrhage caused by surgery.

14. The method of claim 11, wherein the hemorrhagic stroke caused by surgery is a complication of intracerebral hemorrhage caused by surgery and subarachnoid hemorrhage caused by surgery.

15. The method of claim 11, wherein the surgery is a surgery directly involving the central nervous system.

16. The method of claim 15, wherein the surgery is intracranial aneurysmal clipping, embolization, or brain tumor resection.

17. The method of claim 1, wherein the subject is human.

18. The method of claim 1, wherein the hemorrhagic stroke manifests as blood outflowing caused by fracture or breakage of vessel in brain tissue.

* * * * *